United States Patent
Cakmak

(10) Patent No.: US 11,883,155 B2
(45) Date of Patent: Jan. 30, 2024

(54) SYSTEM FOR MONITORING AUDITORY STARTLE RESPONSE

(71) Applicant: Yusuf Ozgur Cakmak, Istanbul (TR)

(72) Inventor: Yusuf Ozgur Cakmak, Istanbul (TR)

( * ) Notice: Subject to any disclaimer, the term of this patent is extended or adjusted under 35 U.S.C. 154(b) by 330 days.

(21) Appl. No.: 17/195,229

(22) Filed: Mar. 8, 2021

(65) Prior Publication Data

US 2021/0186378 A1 Jun. 24, 2021

Related U.S. Application Data

(63) Continuation-in-part of application No. 15/642,287, filed on Jul. 5, 2017, now Pat. No. 10,939,862.

(51) Int. Cl.
| | |
|---|---|
| *A61B 5/11* | (2006.01) |
| *G16H 40/67* | (2018.01) |
| *A61B 5/16* | (2006.01) |
| *A61B 5/1171* | (2016.01) |

(52) U.S. Cl.
CPC .......... *A61B 5/1104* (2013.01); *A61B 5/1176* (2013.01); *A61B 5/162* (2013.01); *G16H 40/67* (2018.01)

(58) Field of Classification Search
CPC ..... A61B 5/1104; A61B 5/1176; A61B 5/162; A61B 5/1103; A61B 5/165; A61B 5/296; A61B 5/6815; A61B 5/6898; A61B 5/0022; G16H 40/67; G16H 50/30

See application file for complete search history.

(56) References Cited

U.S. PATENT DOCUMENTS

| 9,596,544 B1* | 3/2017 | Brotherton | H04R 19/02 |
|---|---|---|---|
| 2014/0065132 A1 | 3/2014 | Hsiao et al. | |
| 2015/0289813 A1 | 10/2015 | Lipov | |
| 2016/0106982 A1 | 4/2016 | Cakmak et al. | |
| 2016/0279435 A1 | 9/2016 | Hyde et al. | |

(Continued)

FOREIGN PATENT DOCUMENTS

| EP | 3756542 A1 | 12/2020 |
|---|---|---|
| WO | WO2007/136901 A2 | 11/2007 |
| WO | WO2012/129465 A1 | 9/2012 |

(Continued)

OTHER PUBLICATIONS

Ćosić, K., et. al. (2016). Multimodal analysis of startle type responses. Computer Methods and Programs in Biomedicine, 129, 186-202. https://doi.org/10.1016/j.cmpb.2016.01.002. (Year: 2016).*

(Continued)

*Primary Examiner* — Eric F Winakur
*Assistant Examiner* — Emily C Clement
(74) *Attorney, Agent, or Firm* — Crowell & Moring

(57) ABSTRACT

A diagnostic system is used for measuring and analyzing startle response of a subject for diagnosis of traumatic brain injuries (TBI) such as concussions. The diagnostic system includes a stimuli delivery circuitry, whereby startle stimuli are delivered to the subject. The diagnostic system comprises at least one sensor circuitry, whereby the startle response of the subject are detected and recorded. The sensor circuitry comprises at least one muscle startle response measuring means, and said diagnostic system comprises a diagnosis circuitry whereby the features of the startle response are extracted and analyzed.

13 Claims, 2 Drawing Sheets

(56) References Cited

U.S. PATENT DOCUMENTS

Figure 1:
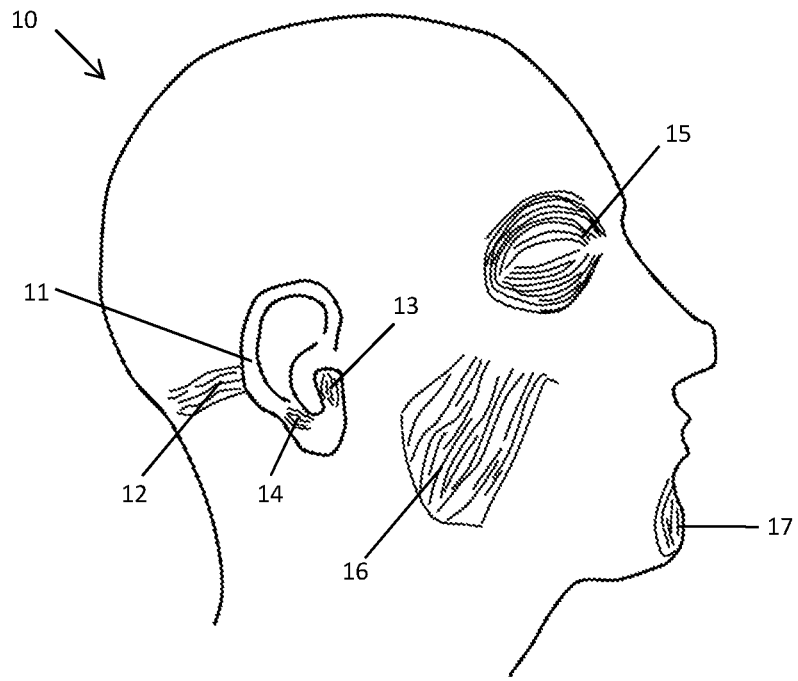

| | | |
|---|---|---|
| 2016/0374594 A1 | 12/2016 | Garcia Molina et al. |
| 2020/0100719 A1 | 4/2020 | Cakmak |

FOREIGN PATENT DOCUMENTS

| | | |
|---|---|---|
| WO | WO2014/179671 A1 | 11/2014 |
| WO | WO2015/129465 A1 | 9/2015 |

OTHER PUBLICATIONS

Benning et al., "Emotional modulation of the post-auricular reflex," dated Oct. 13, 2003, pp. 426-432, Psychophysiology 41 (Jun. 2004) Blackwell Publishing Inc., available at https://www.researchgate.net/publication/8602987.

Braff et al., "Human studies of prepulse inhibition of startle: normal subjects, patient groups, and pharmacological studies," dated Jun. 26, 2001, pp. 234-258, Psychopharmacology 156 (2001).

Chau et al., "Real Time Eye Tracking and Blink Detection with USB Cameras," dated May 12, 2005, pp. 1-11, Boston University Computer Science Technical Report No. 2005-12.

Dichter et al., "Affective Modulation of the Startle Eyeblink and Postauricular Reflexes in Autism Spectrum Disorder," dated Jul. 2010, pp. 858-869, J Autism Dev Disord 40(7) (2010).

Echiverri-Cohen et al., "Analysis of inhibitory functioning in individuals with chronic posttraumatic stress disorder," dated Dec. 20, 2015, pp. 94-103, Elsevier, Journal of Anxiety Disorders 37 (2016).

Freeman et al., "Neural circuitry and plasticity mechanisms underlying delay eyeblink conditioning," dated Aug. 17, 2011, pp. 666-677, Cold Spring Harbor Laboratory Press.

Grillon et al., "A review of the modulation of the startle reflex by affective states and its application in psychiatry," dated May 28, 2003, pp. 1557-1579, Elsevier, National Institute of Mental Health, DHHS, Mood and Anxiety Disorders Program, Clinical Neurophysiology 114 (2003).

Grillon et al., "Baseline startle amplitude and prepulse inhibition in Vietnam veterans with PSTD," Psychiatry Research 64, dated May 5, 1996, pp. 169-178, Elsevier, National Center for Posttraumatic Stress Disorder, Department of Veteran's Affairs Medical Center and Department of Psychiatry, Yale University School of Medicine.

Hess et al., "Postauricular and eyeblink startle responses to facial expressions," dated Jan. 28, 2007, pp. 431-435, Psychophysiology, 44, (2007) Society for Psychophysiological Research, Blackwell Publishing Inc.

Lee et al., "Blink detection robust to various facial poses," dated Aug. 31, 2010, pp. 356-372, Elsevier, Journal of Neuroscience Methods 193 (2010).

Matsuo et al., "Tragicus and Antitragicus Muscles as Constrictors of the External Auditory Meatus," dated 1987, pp. 82-83, European Journal of Plastic Surgery 10 (1987).

O'Beirne et al., "Basic properties of the sound-evoked post-auricular muscle response (PAMR)," dated Aug. 23, 1999, pp. 115-132, Elsevier, Hearing Research 138 (1999).

Shalev et al., "Auditory Startle Response in Trauma Survivors With Posttraumatic Stress Disorder: A Prospective Study," dated Feb. 2000, pp. 255-261, American Journal of Psychiatry 157 (2000).

Zoladz et al., "Current status on behavioral and biological markers of PTSD: A search for clarity in a conflicting literature," dated Mar. 27, 2013, pp. 860-895, Elsevier, Neuroscience and Biobehavioral Reviews 37 (2013).

Gowen et al., "EMG-Free Monitorization of the Acoustic Startle Reflex with a Mobile Phone: Implications of Sound Parameters with Posture Related Resgonses," dated Oct. 22, 2020, p. 5996, vol. 20, No. 21, XP055857521.

Liska et al., "Suppressed acoustic startle response in traumatic brain injury masks post-traumatic stress disorder hyper-responsivity," indicated as dated Aug. 1, 2018, pp. 939-944, vol. 29, No. 11, XP055857693.

International Search Report of the International Searching Authority, dated Nov. 15, 2021, pp. 1-4, issued in International Application No. PCT/TR2021/050201, European Patent Office, Rijswijk, The Netherlands.

* cited by examiner

SYSTEM FOR MONITORING AUDITORY STARTLE RESPONSE

RELATED APPLICATIONS

The present patent document is a continuation-in-part of application Ser. No. 15/642,287, filed Jul. 5, 2017, which is hereby incorporated by reference.

TECHNICAL FIELD

The present disclosure relates to a system whereby the auditory startle response of a subject is determined for diagnosis of traumatic brain injuries (TBI) such as concussions.

BACKGROUND

Traumatic brain injury (TBI) is an important global public health problem. The leading causes of TBI are falls, motor vehicle crashes, struck by or against events, and assaults. In addition, blasts are a leading cause of TBI among active-duty military personnel in war zones. Sports and recreation activities are also a major cause of TBI, including concussions. Traumatic brain injury can result in long-term or lifelong physical, cognitive, behavioral, and emotional consequences. Even mild TBI, including concussion, can cause long-term cognitive problems that affect a person's ability to perform daily activities. Typical acute and/or chronic post-concussive symptoms include physical problems such as headache, dizziness, and visual disturbances; cognitive impairments such as attention, memory, and executive dysfunction; and emotional or behavioral problems such as irritability, anxiety, depression, affective lability, apathy, and/or impulsivity (Langlois, et al. J Head Trauma Rehabil. 2006. 21.5:375-378; Arciniegas, et al. Neuropsychiatr Dis Treat. 2005. 1.4:311-327).

SUMMARY

Current methods of diagnosing concussion typically include self-report and a battery of tests, such as neurocognitive function and balance performance, aimed at evaluating symptoms associated with concussions. However, assessment of emotion responsivity is often difficult because many patients lack insight into their altered personality. In order to overcome this obstacle, a physiological measure of emotion responsivity, such as the startle reflex, can be used. Studies have shown that startle response is suppressed in subjects with mild-to severe TBI, which suggests long-term dysfunction of brainstem neural circuits. Therefore, it is possible to use startle response as a way of measuring cognitive function after TBI and as a diagnostic tool for TBI (Williams and Wood. J Clin Exp Neuropsychol 2012. 34.9: 948-961; Pang, et al. J Neurotrauma. 2015. 32:801-810).

The startle response is a response to abrupt and intense stimulation, consisting of a rapid sequential muscle contraction with the likely purpose of facilitating the flight reaction and/or to protect the body from sudden attack. The startle response consists of a bilateral generalized flexion reflex. Most muscle activity is located in the face and shoulders. Electrophysiological studies have shown that this response is initiated in the medial bulbopontine reticular formation of the lower brainstem. The latencies of both cranial and caudal muscles increase with the distance of their segmental innervation from the brainstem, with the exception of the early EMG activity in the orbicularis oculi muscle. The startle response of the orbicularis oculi muscle consists of two components: an early blink reflex and a later response that is part of the generalized startle reflex. Observing EMG muscle activity during startle responses reveals two subsequent responses. The initial patterned motor reflex, mediated by the caudal brainstem, initiates with activation of the orbicularis oculi (onset latency 20-50 ms), and spreads to the sternocleidomastoid, mentalis, zygomaticus major, zygomaticus minor, masseter, trunk and limb muscles. This response is roughly uniform from time to time and from individual to individual. Different parameters can be used to quantify the auditory startle reflex, including pattern of muscle recruitment, onset latency, muscle response probability and magnitude of the EMG recordings. The blink response onset latencies are between 20 and 100 ms, followed by onset latencies ranging from 30 to 200 ms in face, neck, trunk and limb muscles for the early motor response. The initial motor reflex is followed by a period of decreased activity lasting for about 250-300 ms, after which a second response can be observed, occurring at a latency of about 400-450 ms, lasting from 3 to 10 s or more. An exaggeration of the startle reflex can be expressed in different features, including an excessive EMG burst duration and amplitude, a deviant activation pattern, prolonged onset latencies, a more widespread muscle activation, a lower threshold for response, impaired habituation and occurrence of a second response. Startle response can be used as a tool to investigate human brainstem physiology of the reticulospinal system in health and disease (Brown, et al. Brain. 1991 114:1891-1902, Siegelaar, et al. Experimental brain research. 2006. 174.1: 1-6; Dreissen, et al. Clin Neurophysiol. 2012. 123.1: 34-44).

The exaggerated startle response is generally measured by recording the eyeblink reflex, however, cardiac acceleration and increased electrodermal conductivity of longer latency and duration can also be used. The eyeblink consists of a rapid contraction of the orbicularis oculi muscle which is innervated by the facial nerve. The startle response can be elicited by brief and intense auditory, visual or tactile stimuli with a fast rise time, acoustic startle being the most commonly used. Acoustic startle is evoked by short (50 ms) noises, usually broadband or white noise with a high intensity (90-110 dB). Startle stimuli can be delivered at any time to probe ongoing affective and mental processes. (Grillon and Baas. Clin Neurophysiol. 2003. 114:1557-1579; Shalev et al. Am J Psychiatry. 2000. 157:255-261).

It is known in the art that startle response can be used to assist diagnosis of various conditions in patients. For example, US 2015/289813 (A1), discloses a system and method for the diagnosis of PTSD comprising an electronic device equipped with a built-in or attachable camera, built-in or attachable flash or controllable light source, and a software application. The software application includes a method that records and monitors the diameter of an individual's pupil prior to and after the application of light, using the camera and flash in communication with the electronic device. In another embodiment, the method measures the auditory startle response by measuring the orbicularis oculi response of the individual by electromyography. The method analyzes the data collected and determines the likelihood of individual suffering from PTSD.

Methods and devices utilizing exaggerated startle response as a tool to assist in diagnosing TBIs are also present in the art. An example of such a method may be referred to as WO 2018/213245 (A1), which discloses a device for measuring eyelid movement and/or pupillary response in a human subject comprising at least one stimulator to provide mechanical, light, acoustic and/or electrical stimuli to the subject and a camera to monitor the resulting blinking response of the subject. The device can be used to diagnose TBIs, such as concussions.

However, it may not always be possible to measure the eyeblink response of a subject, especially immediately after the occurrence of a brain injury as the patient may not be able to open their eyes for the measurements to be taken. In these cases, the eyeball movements when the eyelid is closed as well as the movements of the facial (mimetic and swallowing muscles), neck muscles (e.g. sternocleidomastoid muscle) and shoulder muscles (e.g. trapezius muscle), collectively referred to as the muscle startle response (MSR), can be used to measure the startle response due to being part of the same circuitry as mentioned above (Castellote, et al. Exp Brain Res. 2007. 177:129-136; Jancke, et al. Int J Psychophysiol. 1996. 22:85-96; Bisdorff, et al. Electroencephalogr Clin Neurophysiol. 1994. 93:409-416).

Another alternative measure of exaggerated startle response is the post-auricular muscle response (PAMR). PAMR is a large sound-evoked vestigial muscle response that acts to pull the ear backward, which can be evoked by clicks or tone-bursts. Currently, PAMR is mostly used as a clinical tool to test hearing due to the speed and ease with which the response can be obtained (O'Beirne and Patuzzi. Hearing Res. 1999. 138:115-132).

An example of hearing-related use of PAMR may be referred to as WO 2012/129465 (A1) which discloses an arrangement for custom fitting a hearing prosthesis system, such as cochlear implant systems, to a patient to optimize its operation. The PAMR measurement determines a PAMR of the patient to an auditory stimulus signal. For example, the PAMR may include a PAMR amplitude growth function or a PAMR threshold stimulus level at which a PAMR is measured in the patient. Then a patient fitting module sets an operating characteristic of the hearing prosthesis system based on the PAMR response.

Another example may be referred to as WO 2007/136901 (A2), which discloses a device and method for objectively measuring tinnitus in human and animal subjects. The startle reflex is induced by exposing a subject to an alteration in a sound pattern otherwise qualitatively similar to the subject's tinnitus. The subject's acoustic startle response is obtained and used to determine whether the subject detected the alteration of the sound pattern. The device comprises a controller for selecting a primary sound pattern and selecting a reflex stimulus sound pattern, a generator for generating signals associated with the sound patterns selected by the controller, a transducer for converting the generated signals to the selected sound patterns and exposing the selected sound patterns to the subject and a response sensor for detecting a response by the subject to the selected reflex stimulus sound pattern.

The inventors of the present system have also discovered an additional alternative measure of exaggerated startle response, which is the intrinsic auricular muscle response (IAMR). Intrinsic auricular muscles comprise helicis major, helicis minor, tragicus and antitragicus muscles. It is known that the tragicus and antitragicus muscles cooperate to constrict the external auditory meatus as the orbicularis oculi muscle constricts the palpebral fissure (Matsuo and Hiroshe. Eur J Plast Surg. 1987. 10:82-83). This is thought to be due to the eyeblink pathway wherein eyelid movement is generated by the facial motor nucleus (Freeman and Steinmetz. Learn Mem. 2011. 18:666-677). Facial nerve additionally innervates the muscles of the auricle. As a result, signals for movement of the orbicularis oculi transmitted by the facial nerve also reach the tragicus and antitragicus muscles, causing the constriction of the external auditory meatus. Therefore, it is possible to determine the startle response by measuring the intrinsic auricular muscle response (IAMR) of the subject. It is also possible to use helicis major, helicis minor muscles for this purpose.

The present system aims to provide a system whereby the acoustic startle reflex, namely muscle startle response, IAMR and PAMR, of a subject are measured in order to present an effective and inexpensive method for diagnosing brain damage, including but not limited to TBI and strokes.

The present system provides a diagnostic system.

The acoustic startle reflex of a subject is measured by the system in order to present an effective and inexpensive method for diagnosing brain damage, including but not limited to TBI and strokes.

At least one of startle muscle startle response, PAMR and IAMR of a subject can be measured and analyzed by the system in order to present a corroborative, effective and inexpensive method for diagnosing brain damage, including but not limited to TBI and strokes.

BRIEF DESCRIPTION OF THE TECHNICAL DRAWINGS

The accompanying drawings are given solely for the purpose of exemplifying a diagnostic system, whose advantages over prior art were outlined above and will be explained in brief hereinafter.

The drawings are not meant to delimit the scope of protection, nor should they be referred to alone in an effort to interpret the scope without recourse to the technical disclosure in the description.

FIG. 1 demonstrates some of the anatomical structures of the human head.

Figure 2:
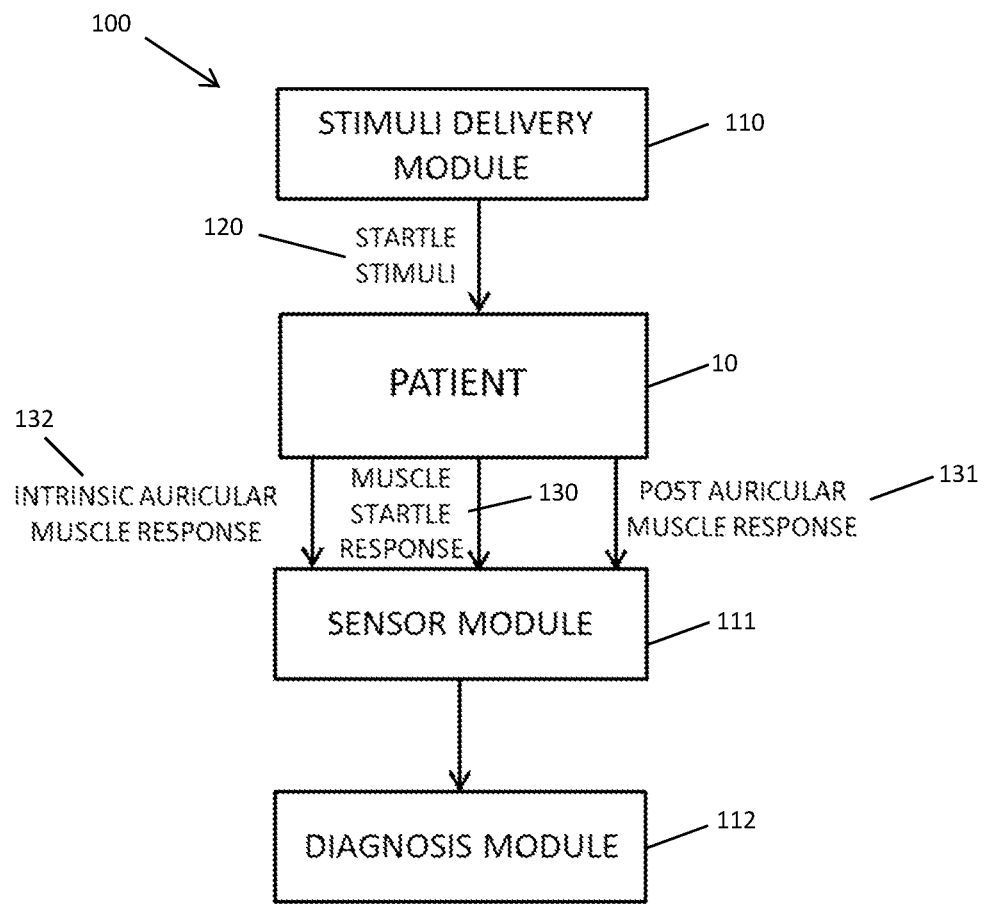

FIG. 2 demonstrates a block diagram of a diagnostic system.

Figure 3:
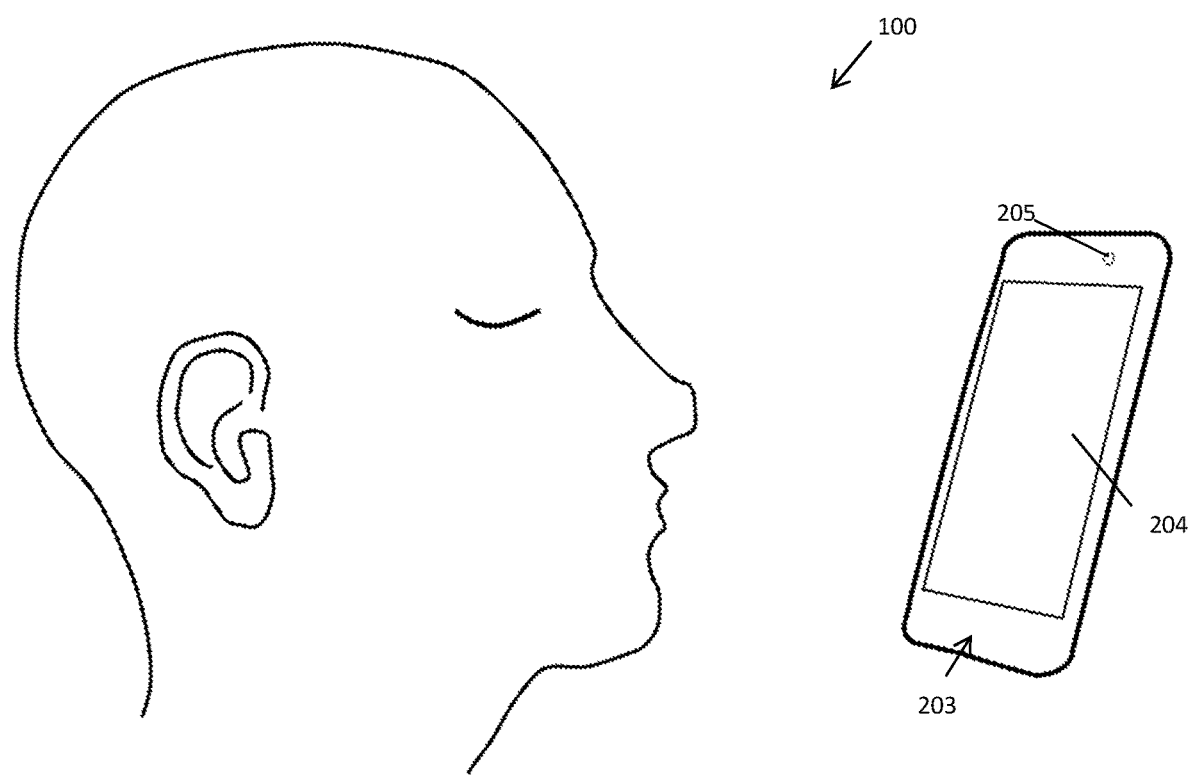

FIG. 3 demonstrates a schematic view of one embodiment of a diagnostic system.

DETAILED DESCRIPTION

The following numerals are referred to in the detailed description:
10 Subject
11 Pinna
12 Post-auricular muscle
13 Tragicus muscle
14 Antitragicus muscle
15 Orbicularis oculi muscle
16 Masseter muscle
17 Mentalis muscle
100 Diagnostic system
110 Stimuli delivery module or circuitry
111 Sensor module or circuitry
112 Diagnosis module or circuitry
120 Startle stimuli
130 Muscle startle response
131 Post-auricular muscle response
132 Intrinsic auricular muscle response
203 Smartphone
204 Screen
205 Camera A diagnostic system (100) includes a stimuli delivery module (110), whereby startle stimuli (120) are delivered to subject (10); at least one sensor module (111), connected to at least one camera, whereby the startle response, i.e. at least one of the MSR (130), PAMR (131) and IAMR (132) of subject (10) are detected and recorded; and a diagnosis module (112) whereby the features of the startle response of subject (10) are extracted and classified by a software application comprising a facial recognition software (not shown) as will be delineated hereinafter (FIG. 2).

As mentioned above, muscle startle response (130) comprises the response of facial, neck muscles and shoulder muscles to acoustic startle stimuli. More specifically, facial muscles comprise mimetic (including but not limited to orbicularis oculi, mentalis, zygomaticus major and zygomaticus minor muscles) and swallowing (including but not limited to masseter muscle) muscles. Neck muscles comprise, including but not limited to, the sternocleidomastoid muscle. Shoulder muscles comprise, including but not limited to, trapezius muscle.

The brainstem houses cranial nerves. These cranial nerves are distributed to three different subsections of the brainstem: midbrain, pons and medulla oblongata. The midbrain houses oculomotor (III cranial nerve) and trochlear (IV) nerves, which are responsible for the medial, inferior, superior or combined movements of the eyeball. The lateral movement of the eyeball is under the control of Abducens Nerve (VI) which originates at the pons. Other cranial nerves trigeminal nerve (V), facial nerve (VII) and vestibulocochlear nerve (VIII) also originate from the pontine level. At the level of medulla oblongata, glossopharyngeal nerve (IX), vagus nerve (X), accessory nerve (XI) and hypoglossal nerve (XII) originate. These cranial nerves and the muscles they are connected to can be used as a proxy to determine the integrity of the brainstem and its cortical connections can be tested with non-invasive systems in order to determine any damage therein. The diagnostic system (100) provides a way to determine the presence and location of damage to the brainstem of a subject by measuring the possible deviation and/or latency of the acoustic startle reflex, namely at least one of MSR, PAMR and IAMR, of said subject. For example, a deviation or latency in startle response in masseter (V), orbicularis oculi, mentalis, zygomaticus major and zygomaticus minor (VII) and sternocleidomastoid and trapezius (XI) muscles indicate a problem with the corresponding portion of the brainstem and the upper spinal cord he related cranial nerves originated from. Diagnostic system (100) can also provide a response battery, or a diagnostic matrix comprising of individual muscle startle responses as well as PAMR and IAMR where available, where data is collected in order to get a full picture of the extent of damage in the brainstem and the upper spinal cord.

Diagnostic system (100) can work in conditions where the subject has their eyes closed to detect and trace/monitor eyeball movements, including but not limited to saccades, smooth pursuit movements, vergence movements and vestibulo-ocular movements, over the eyelid skin based on skin distortions, including responses to acoustic stimuli. Such responses help to understand the integrity of the vestibulocochlear nerve to cranial nerves of extraocular muscles (oculomotor nerve, trochlear nerve and abducens nerve). In the eyelids-closed case, the direction of the movement dysfunction (lateral, medial, superior, inferior and combinations) as a response to acoustic stimuli that can be detected with a camera can allow to detect the dysfunctional cranial nerve(s) and therefore the injured level of the brainstem (midbrain, pons, medulla oblongata). In the eyelids-closed case, the integration of the abovementioned eye movement responses with the acoustic startle response (a reflex from vestibulocochlear nerve to facial nerve) that results with the movement of the skin surrounding the orbit and eye (as a result of orbicularis oculi contraction) allows to differentiate midbrain injuries from pontine and medulla oblongata injuries with the aid of a camera that can detect eyeball movements and skin movements.

The same system can be used to detect overall facial, neck and/or shoulder skin movements that are formed by muscle startle responses as a response to acoustic startle stimuli. This response can be retrieved from a specific region out of the orbital zone, from any facial (mimetic and swallowing muscles), neck (e.g. sternocleidomastoid muscle) and shoulder (e.g. trapezius muscle) region that can move the skin. The acoustic startle response can be retrieved from muscle startle response only or in combination with ear movements (IAMR and PAMR) with the aid of camera-based analyses.

In an alternative embodiment of the case, the camera system is able to detect shoulder movements, which are controlled by the accessory nerve, as a response to acoustic startle reflex to determine the integrity of medulla oblongata and upper spinal cord. The response amplitude, velocity, acceleration of the skin movement, range of skin movement and delayed-time like different responses can be analyzed for each response in order to for a response battery, or a diagnostic matrix.

Diagnostic system (100) use all of the abovementioned responses for a meta-analyses and localization of the injury.

Diagnostic system (100) can be used in eyelids-closed cases to determine the neurological and psychological conditions present in the subject.

In an alternative embodiment, IAMR and PAMR to acoustic startle stimuli may be measured by capturing and analyzing movement and delayed-time like different responses of the ear using a camera.

Simultaneous measurement of muscle startle response (130) and IAMR (132) allows for the muscle response data and IAM data to be correlated in order to generate a response battery or diagnostic matrix to determine the relationship between muscle startle response (130) and IAMR (132). The index compiled from the correlation of muscle response and IAMR data will also have the advantage of providing noise reduction in startle response measurements. In an alternative embodiment, IAMR (132) can be recorded b by placing electrodes on the tragicus (13) and antitragicus muscles (14) and PAMR by placing electrodes on the post-auricular muscle (12) of the subject (10) respectively, with a bandwidth from 10 to 300 Hz.

The diagnostic system (100) measures the auditory startle response (130, 131, 132) of a subject (10). Auditory startle response (130, 131, 132) is measured by stimuli delivery module (110), which is circuitry, by delivering startle stimuli (120) to subject (10). Startle stimuli (120) are delivered by playing a sudden, loud tone or noise, such as a sound burst of 95 decibels, for subject (10) preferably using earphones. Startle stimuli (120) can be provided by 3D surround system with spatial component (for example as if the sound is coming from the right front or left back direction) to induce a search response to induce eyeball movements. An emotional component can be embedded into spatially designed auditory stimuli to induce a search reflex towards the auditory stimuli. For example, the auditory stimuli can be an imaginary walk through of a previously known environment, such as a walk through the subject's home, to induce eyeball movements. In an alternative embodiment, startle stimuli (120) can be provided by earphones placed in the subject's ear.

Diagnostic system (100) also includes a sensor module (111), which is circuitry, comprising plurality of sensors (not shown). The sensors are configured to monitor and record a plurality of different physiological responses to subject's (10) exposure to stimuli output (120, 121), such as MSR (130), PAMR (131) and IAMR (132). The physiological response data are collected during the subject's (10) exposure to the stimuli.

Sensor module (111) detects the subject's (10) response to startle stimuli (120) by monitoring the subject's (10) movement of muscles (muscle startle response (130)). In one embodiment, sensor module (111) detects muscle startle response (130) by recording the muscle startle response (130) of the subject (10) by a camera and measuring its speed and amplitude and analyzing through a facial recognition software. This can be achieved by any method present in the art that are known to the skilled person.

In an alternative embodiment, sensor module (111) also comprises at least one electrode designed to be placed on the back of the ear corresponding to post-auricular muscle (12) to measure the PAMR (131) of subject (10) simultaneously while measuring the muscle startle response (130), thereby increasing accuracy. Preferably, sensor module (111) comprises two electrodes to be placed one on the back of the ear of subject (10) directly over post-auricular muscle (12) and one directly adjacent on pinna (11) of subject (10) and a grounding electrode to be placed elsewhere on subject's (10) head. The PAMR (131) may be determined on one side, either ipsilateral or contralateral, of the subject (10), or on both sides of the subject (10). Additionally, sensor module (111) may comprise a sensor such as an EMG sensor detecting the electric potential generated by the tragicus muscle (13) and antitragicus muscle (14) in order to measure the IAMR (132) of the subject. The sensor may comprise surface electrodes (surface EMG) or needle-shaped electrodes (intramuscular EMG). In one embodiment, needle-shaped electrodes are pricked on the auricular skin and reaches said tragicus muscle (13) and antitragicus muscle (14).

The MSR (130), PAMR (131) and IAMR (132) data are collected by sensor module (111) and transmitted to diagnosis module (112). Diagnosis module (112), which is circuitry, can be in wired or wireless communication with sensor module (111). Diagnosis module (112) comprises a software application for analyzing data which can include the amplitude and speed of response (130, 131, 132) to determine whether the individual is suffering from TBI.

Diagnosis module (112) may also determine a threshold value depending on at least one of the age, ethnic background, sex and baseline response of subject (10). In some embodiments, diagnosis module (112) combines and applies weights to the processed extracted features and compares the combined value to the threshold. The weighted features can be combined by any arithmetic process. In such embodiments, diagnosis module (110) identifies subject (10) as having TBI if the combined value is above the threshold, and not having TBI if the combined value is below the threshold.

In some embodiments, diagnostic system (100) may be coupled to a network interface configured for wired or wireless data communications, and the results may be transmitted to a remote computing system over a computer network and displayed to a clinician, care provider and/or subject (10) by outputting the results via a display device concurrently or after the fact.

In some embodiments, diagnostic system (100) can comprise a mobile electronic device, such as a smartphone, tablet, PC computer or any other like device known in the art.

Diagnostic system (100) allows startle response (130, 131, 132) to be monitored over time (long-term monitoring) and also emotional state of the subject (10) at that moment to be determined.

FIG. 3 illustrates an embodiment of diagnostic system (100). Diagnostic system (100) comprises a smartphone (203) equipped with a screen (204) and a built-in camera (205) a mobile application (not shown) for the analysis of data. Camera (205) is used to monitor the face of subject (10) to determine the startle response (130, 131, 132) to startle stimuli (120).

The methods, devices, processing, circuitry, and logic described above may be implemented in many different ways and in many different combinations of hardware and software. For example, all or parts of the implementations may be circuitry that includes an instruction processor, such as a Central Processing Unit (CPU), microcontroller, or a microprocessor; or as an Application Specific Integrated Circuit (ASIC), Programmable Logic Device (PLD), or Field Programmable Gate Array (FPGA); or as circuitry that includes discrete logic or other circuit components, including analog circuit components, digital circuit components or both; or any combination thereof. The circuitry may include discrete interconnected hardware components or may be combined on a single integrated circuit die, distributed among multiple integrated circuit dies, or implemented in a Multiple Chip Module (MCM) of multiple integrated circuit dies in a common package, as examples.

Accordingly, the circuitry may store or access instructions for execution, or may implement its functionality in hardware alone. The instructions may be stored in a tangible storage medium that is other than a transitory signal, such as a flash memory, a Random Access Memory (RAM), a Read Only Memory (ROM), an Erasable Programmable Read Only Memory (EPROM); or on a magnetic or optical disc, such as a Compact Disc Read Only Memory (CDROM), Hard Disk Drive (HDD), or other magnetic or optical disk; or in or on another machine-readable medium. A product, such as a computer program product, may include a storage medium and instructions stored in or on the medium, and the instructions when executed by the circuitry in a device may cause the device to implement any of the processing described above or illustrated in the drawings.

The implementations may be distributed. For instance, the circuitry may include multiple distinct system components, such as multiple processors and memories, and may span multiple distributed processing systems. Parameters, databases, and other data structures may be separately stored and managed, may be incorporated into a single memory or database, may be logically and physically organized in many different ways, and may be implemented in many different ways. Example implementations include linked lists, program variables, hash tables, arrays, records (e.g., database records), objects, and implicit storage mechanisms. Instructions may form parts (e.g., subroutines or other code sections) of a single program, may form multiple separate programs, may be distributed across multiple memories and processors, and may be implemented in many different ways. Example implementations include stand-alone programs, and as part of a library, such as a shared library like a Dynamic Link Library (DLL). The library, for example, may contain shared data and one or more shared programs that include instructions that perform any of the processing described above or illustrated in the drawings, when executed by the circuitry.

The invention claimed is:

1. A diagnostic system for measuring and analyzing startle response of a subject comprising:
   a stimuli delivery circuitry configured to deliver startle stimuli to said subject;
   at least one sensor circuitry configured to detect and record a startle response of said subject;
   at least one camera connected to said sensor circuitry and configured to capture at least part of said startle response of said subject by capture of movement of facial muscles of said subject during said startle response; and
   a diagnosis circuitry configured to extract and analyze features of said startle response,
   wherein said startle response of said subject being detected by said sensor circuitry and/or said camera comprises at least one of a muscle startle response, a post-auricular muscle response or an intrinsic auricular muscle response; and
   said diagnosis circuitry is in communication with a memory having stored thereon a software application that when executed by said diagnosis circuitry generates a response battery comprising startle responses from individual muscles and based on said analysis of said features of said startle responses determines a location of damage to a brainstem of said subject.

2. The diagnostic system as set forth in claim 1, wherein said startle response of said subject detected by said sensor circuitry and said camera comprises said muscle startle response.

3. The diagnostic system as set forth in claim 2, wherein said startle response of said subject that are detected by said sensor circuitry and said camera comprises said muscle startle response, said post-auricular muscle response and said intrinsic auricular muscle response.

4. The diagnostic system as set forth in claim 1, wherein said startle stimuli is a sudden, loud, tone or noise.

5. The diagnostic system as set forth in claim 4, wherein said startle stimuli is a sound burst of 95 decibels.

6. The diagnostic system as set forth in claim 1, wherein said startle stimuli is provided by a three dimensional (3D) surround system with a spatial component.

7. The diagnostic system as set forth in claim 6, wherein said startle stimuli is a spatially designed auditory stimuli to induce a search reflex towards said startle stimuli.

8. The diagnostic system as set forth in claim 1, wherein said sensor circuitry and said diagnosis circuitry are in wireless communication.

9. The diagnostic system as set forth in claim 1, wherein said software application, when executed by said diagnostic circuitry, is further configured to provide face recognition.

10. The diagnostic system as set forth in claim 9, wherein said startle response data comprises an amplitude, a speed and a latency of response of said subject.

11. The diagnostic system as set forth in claim 9 wherein said diagnostic system is in wired or wireless communication with a network interface and said extracted and analyzed startle response data are communicated to a clinician, care provider and/or subject via said network interface.

12. The diagnostic system as set forth in claim 9 wherein said diagnostic system is in wired or wireless communication with a network interface and said extracted and analyzed startle response data are communicated via said network interface for output via a display device concurrently or after the fact.

13. The diagnostic system as set forth in claim 1, further comprising a mobile electronic device, said mobile electronic device comprising one or more of a smartphone, a tablet or a personal computer (PC).

* * * * *